(12) United States Patent
Postma (10) Patent No.: US 8,739,786 B2
(45) Date of Patent: Jun. 3, 2014

(54) PORTABLE HAND-HELD VAPORIZER HEATING ASSEMBLY

(75) Inventor: Herbert F. Postma, Boca Raton, FL (US)

(73) Assignee: Vaporfection International, Inc., Deerfield Beach, FL (US)

( * ) Notice: Subject to any disclaimer, the term of this patent is extended or adjusted under 35 U.S.C. 154(b) by 235 days.

(21) Appl. No.: 13/430,312

(22) Filed: Mar. 26, 2012

(65) Prior Publication Data

US 2013/0247910 A1    Sep. 26, 2013

(51) Int. Cl.
*A61M 11/00* (2006.01)

(52) U.S. Cl.
USPC ................................ 128/203.26; 128/203.23

(58) Field of Classification Search
CPC ............. A61M 16/16; A61M 11/041; A61M 2205/8206; A61M 15/06
USPC ............. 128/203.26, 203.27, 200.11–200.13, 128/202.21, 203.12, 204.13, 203.23; 131/273
See application file for complete search history.

(56) References Cited

U.S. PATENT DOCUMENTS

| | | | | |
|---|---|---|---|---|
| 1,405,802 A | * | 2/1922 | Phelan et al. | 128/203.28 |
| 5,144,962 A | * | 9/1992 | Counts et al. | 131/194 |
| 5,269,327 A | * | 12/1993 | Counts et al. | 131/194 |
| 6,125,853 A | * | 10/2000 | Susa et al. | 131/273 |
| 6,446,426 B1 | * | 9/2002 | Sweeney et al. | 60/39.81 |
| 6,990,978 B2 | * | 1/2006 | Shayan | 128/203.27 |
| 7,100,618 B2 | * | 9/2006 | Dominguez | 131/273 |
| 7,186,958 B1 | * | 3/2007 | Nelson | 219/533 |
| 7,665,460 B2 | * | 2/2010 | Lindsay et al. | 128/200.14 |
| 7,997,280 B2 | * | 8/2011 | Rosenthal | 131/191 |
| 8,291,918 B2 | * | 10/2012 | Magnon | 131/271 |
| 8,314,591 B2 | * | 11/2012 | Terry et al. | 320/114 |
| 8,550,068 B2 | * | 10/2013 | Terry et al. | 128/202.21 |
| 2008/0023003 A1 | * | 1/2008 | Rosenthal | 128/203.26 |
| 2008/0149118 A1 | * | 6/2008 | Oglesby et al. | 131/194 |
| 2011/0126831 A1 | * | 6/2011 | Fernandez Pernia | 128/203.27 |
| 2013/0152922 A1 | * | 6/2013 | Benassayag et al. | 128/202.21 |
| 2013/0228170 A1 | * | 9/2013 | Alper | 128/202.21 |

* cited by examiner

*Primary Examiner* — Steven Douglas
(74) *Attorney, Agent, or Firm* — The Concept Law Group, P.A.; Scott D. Smiley; Yongae Jun (57) ABSTRACT

A portable hand-held vaporizer assembly that has a body shaped to fit substantially within a standard-sized clothing pocket with the body including an airflow chamber defining an airflow passage and having a proximal end and a distal end, opposite to the proximal end, defining a distal opening that places the airflow passage in fluid communication with an outside environment, the airflow chamber being at least partially encapsulated within the body. The body further having a convection-based heating element assembly with a heating element having a portion thermally coupled to the airflow passage, a herb placement zone in fluid communication with the airflow passage, and a conductive conduit that places the airflow passage in fluid communication with the outside environment, with a first position where a distal end of the conduit is substantially recessed within the body and second position where the distal end extends a length away from the body.

20 Claims, 6 Drawing Sheets

PORTABLE HAND-HELD VAPORIZER HEATING ASSEMBLY

FIELD OF THE INVENTION

The present invention relates generally to a vaporizer for inhalation of active ingredients within a plant material, and more particularly relates to a portable, concealable, hand-held, vaporizer utilizing convection heating that provides vapor for inhalation.

BACKGROUND OF THE INVENTION

A vaporizer is a device used to extract the active ingredients of plant material, e.g., tobacco, or other herbs or blends, for inhalation by a human. Vaporization involves heating a material so that its active compounds boil off into a vapor. As opposed to smoking, i.e., burning, vaporization avoids the production of irritating, toxic, and carcinogenic by-products. In fact, no combustion occurs, so no smoke or taste of smoke is present. Studies show that vapor contains substantially zero particulate matter or tar, and, in comparison to smoking, significantly lower concentrations of noxious gases such as carbon monoxide. It has also been shown that, in comparison to other drug delivery methods, such as ingestion, vaporization has a more rapid onset of pharmacological effect, direct delivery into the bloodstream (via the lungs), and more precise titration such that the desired level is reached and not exceeded, enabling consistent and appropriate dosage.

Generally, those vaporizers utilizing convection-based heating methods employ the use of a heating element by which air passes through, or is in contact with, such that the temperature of the air is heated sufficiently to extract an herb's natural ingredients. To remove an herb's active ingredients the effective vapor temperature varies depending on the type of supplied herb, but generally ranges from 350 to 400 degrees Fahrenheit. After the active ingredients from the herb are boiled off into a vapor, it generally is too hot to be comfortably and/or safely inhaled by a human being. As such, many vaporizes utilize hoses (also called "whips"), elongated chambers, and large heat sinks to reduce the temperature of the vapor so it is safe and comfortable for human inhalation. For most known vaporizers, the vaporization process requires an assembly or casing that is cumbersome and not easily portable. Those assemblies that are portable are too large to conceal within a standard-sized pant pocket and do not allow the device to be effectively and conveniently transported. Most of these vaporizes also require the unit to be plugged in to an electric outlet, which is inconvenient for those persons without access to electricity.

To effectively reduce the temperature of the vapor so it can be consumed, many hand-held vaporizers utilize an elongated chamber that reduces the vapor to a desired temperature. This elongated chamber commonly creates an assembly that is in the general shape of a flashlight with a nozzle-type mouthpiece at the end. There are numerous disadvantages associated with the elongated shape of the vaporizer. With the mouthpiece coupled to the end of the device it becomes readily identifiable as a smoking-type apparatus, which many users find undesirable. Few, if any, of those hand-held vaporizers easily conceal the mouth piece, without removal into multiple components, which can be easily misplaced and/or dropped. As most mouth pieces are not easily concealable, and because they generally have at least one opening disposed to the outside environment to inhale the vapor, the device also becomes susceptible to liquids and debris from entering, which may contaminate the device's functionality. Those vaporizers that are shaped in an elongated fashion also typically require the vaporizer to be subject to the time-intensive task of disassembling it into multiple components in order for the user to insert the herbs. As such, few vaporizers allow a user to insert and remove herbs into the vapor chamber quickly and efficiently without at least partially disassembling the device.

To allow the vapor temperature to reduce to comfortable and safe ranges, many known vaporizers have their heating element at a location 4-6 inches away from the mouthpiece or inhaling area. In such configurations, which are in-line with most known vaporizers that are elongated, the vapor is given more time to dissipate the heat. This, however, negatively creates an inconsistent temperature at the mouthpiece that is dependent on the inhaling rate of the user. For example, as a user inhales faster, the air from the outside environment passes more quickly past the heating element which in turn reduces the temperature at the mouthpiece. A slower inhale rate produces a higher temperature at the mouthpiece because the incoming air is in contact with the heating element longer. This can lead to a less effective release of the active ingredients in the herbs, should the user inhale very fast. Furthermore, as the temperature generally varies, depending on the inhaling rate, many hand-held vaporizers require a user to inconveniently adjust their breathing rate to produce the desired temperature at the mouth piece. As the temperature generally varies, most known portable hand-held vaporizers do not allow the user to have an optimized air flow, a safe vapor temperature at the mouth piece, and a highly potent vapor containing the herb's active ingredients.

To compensate for the sporadic temperature at the mouthpiece and to form a more compact body of the vaporizer, many known vaporizers utilize conduction-based, as opposed to convection-based, heating, i.e. direct contact of the herb with a heated material. These known vaporizers overcome sporadic vapor temperatures by placing the heating element closer to the mouthpiece. These vaporizers are able to accomplish this as there is no fluid that is required to be heated. Conduction vaporizers have their own set of problems, however, and are generally considered inferior to convection-based heated vaporizers. Convection heating is more efficient as the heated fluid, "air," is in contact with more surface area of the herb. This in turn provides a more potent vapor and does not require the user to adjust the herbs. Convection-based heating vaporizers further allow a user to control the heating element more effectively than those conventional conduction-based heated vaporizers. This also allows for a generally more potent vapor, as the user increases the chances that all of the herb's active ingredients are boiled off into the vapor. As such, few, if any, known vaporizers are able to utilize convection heating into a compact discrete design that creates safe and comfortable vapor temperatures.

Therefore, a need exists to overcome the problems with the prior art as discussed above.

SUMMARY OF THE INVENTION

The invention provides a portable hand-held vaporizer assembly that overcomes the hereinafore-mentioned disadvantages of the heretofore-known devices and methods of this general type and provides a device that utilizes convection-based heating, while producing vapors for a user to inhale at a safe and comfortable temperature. The invention also provides a portable vaporizer that is discrete and not readable identifiable to the viewing public and easily transportable within a pant or other type of pocket, e.g., shirt, jacket, etc., of a user.

With the foregoing and other objects in view, there is provided, in accordance with the invention, a portable hand-held vaporizer assembly that includes a body shaped to fit substantially within a standard-sized clothes pocket, e.g., 10"×8", with the body that has an airflow chamber defining an airflow passage, the air flow chamber having a proximal end and a distal end, opposite to the proximal end, the distal end defining a distal opening that places the airflow passage in fluid communication with an outside environment and being at least partially encapsulated within the body. The body further has a heating element assembly having a portion thermally coupled to the airflow passage, an herb placement zone in fluid communication with the airflow passage, and a conductive conduit that places the airflow passage in fluid communication with the outside environment, the conduit having a first position where a distal end of the conduit is substantially placed within the body and a second position where the distal end extends a length away from the body.

In accordance with another feature, one embodiment of the present invention includes the body with an upper end, a lower end, opposite to the upper end, and a body height separating the upper and lower end that is at most approximately 6 inches.

In accordance with a further feature of the present invention, the body is in the general shape of a standard-sized cellular phone.

In accordance with yet another feature, an embodiment of the present invention includes the herb placement zone having a screen that separates the herb placement zone from the airflow channel and an upper edge that is at most approximately 2 inches away from a lower portion of the conduit.

In accordance with one feature of the present invention, the conduit is metallic.

In accordance with yet another feature of the present invention, the conduit has a substantially non-conductive mouthpiece coupled thereto.

In accordance with another feature of present invention, the substantially non-conductive mouthpiece is adjustable a variable length away from the distal end of the conduit.

In accordance with one more feature of the present invention, body includes a cover that is coupled to the body and removably-couplable to a portion of the conduit when the conduit is in either in either the first or second positions.

In accordance with a further feature of the present invention, the cover is rotatable and made from a conductive material.

In accordance yet another feature of the present invention, the conduit is rotatable along a rotation path, defined by the conduit, to either the first position or the second position.

In accordance with an additional feature of the present invention, the conduit is slidably-rotatable to either the first position or the second position.

In accordance with one more feature of the present invention, the conduit is slidable along a translation path defined by the conduit to either the first position or the second position.

In accordance with a further feature of the present invention, the conduit is operable to be placed in a third position that at least partially exposes the herb placement zone.

In accordance with another feature, an embodiment of the present invention includes a body shaped to fit substantially within a standard-sized pocket that includes a multidirectional airflow chamber defining a multidirectional airflow passage, the multidirectional airflow chamber that has a proximal end, a distal end, opposite to the proximal end, and a chamber length separating the proximal and distal ends, the distal end defining a distal opening that places the multidirectional airflow passage in fluid communication with an outside environment. The multidirectional chamber also has at least two separate portions along a chamber length that at least partially overlap one another and is at least partially encapsulated within the body. The body further includes a heating element assembly having a portion thermally coupled to the multidirectional airflow passage, an herb placement zone in fluid communication with the multidirectional airflow passage, and a conductive conduit that places the multidirectional airflow passage in fluid communication with the outside environment.

In accordance an additional feature of the present in invention, the body has a lower end, an upper end, opposite to the lower end, and a body height separating the lower end and the upper end, wherein the chamber length is greater than the body height.

In one more embodiment of the present invention, the assembly has a body that defines an inner area, with the body having a lower end, an upper end, and a body length of at most approximately 6 inches separating the lower end and upper end, a multidirectional airflow chamber defining a multidirectional airflow passage, with the multidirectional airflow chamber having a proximal end and a distal end, opposite to the proximal end, the distal end defining a distal opening that places the multidirectional airflow passage in fluid communication with an outside environment and being at least partially encapsulated within body. The body further includes a heating element assembly having a portion thermally coupled to the multidirectional airflow passage, an herb placement zone in fluid communication with the multidirectional airflow passage, and a conductive conduit coupled to the body that places the multidirectional airflow passage in fluid communication with the outside environment, the conduit being operable to be either slidable or rotatable to a first position where the body substantially conceals the conduit and a second position where the conduit extends outwardly away from the inner area.

Although the invention is illustrated and described herein as embodied in a vaporizer heating assembly, it is, nevertheless, not intended to be limited to the details shown because various modifications and structural changes may be made therein without departing from the spirit of the invention and within the scope and range of equivalents of the claims. Additionally, well-known elements of exemplary embodiments of the invention will not be described in detail or will be omitted so as not to obscure the relevant details of the invention.

Other features that are considered as characteristic for the invention are set forth in the appended claims. As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one of ordinary skill in the art to variously employ the present invention in virtually any appropriately detailed structure. Further, the terms and phrases used herein are not intended to be limiting; but rather, to provide an understandable description of the invention. While the specification concludes with claims defining the features of the invention that are regarded as novel, it is believed that the invention will be better understood from a consideration of the following description in conjunction with the drawing figures, in which like reference numerals are carried forward. The figures of the drawings are not drawn to scale.

Before the present invention is disclosed and described, it is to be understood that the terminology used herein is for the purpose of describing particular embodiments only and is not intended to be limiting. The terms "a" or "an," as used herein, are defined as one or more than one. The term "plurality," as used herein, is defined as two or more than two. The term "another," as used herein, is defined as at least a second or more. The terms "including" and/or "having," as used herein, are defined as comprising (i.e., open language). The term "coupled," as used herein, is defined as connected, although not necessarily directly, and not necessarily mechanically.

As used herein, the terms "about" or "approximately" apply to all numeric values, whether or not explicitly indicated. These terms generally refer to a range of numbers that one of skill in the art would consider equivalent to the recited values (i.e., having the same function or result). In many instances these terms may include numbers that are rounded to the nearest significant figure. In this document, the term "longitudinal" should be understood to mean in a direction corresponding to an elongated direction of the heating element. The term "heating element," as used herein, indicates a structure that actively produces heat and are directly physically coupled to such structures, as opposed to nearby structures that receive heat via convection and possibly transfer heat to other areas. The term "downstream," as used herein indicates a location along a path of flow that is further down the path of flow and occurs after a reference point in that path of flow.

BRIEF DESCRIPTION OF THE DRAWINGS

The accompanying figures, where like reference numerals refer to identical or functionally similar elements throughout the separate views and which together with the detailed description below are incorporated in and form part of the specification, serve to further illustrate various embodiments and explain various principles and advantages all in accordance with the present invention.

DETAILED DESCRIPTION

While the specification concludes with claims defining the features of the invention that are regarded as novel, it is believed that the invention will be better understood from a consideration of the following description in conjunction with the drawing figures, in which like reference numerals are carried forward. It is to be understood that the disclosed embodiments are merely exemplary of the invention, which can be embodied in various forms.

The present invention provides a novel and efficient portable hand-held vaporizer assembly that provides the discreteness and transportability that many users desire along with the effectiveness and efficiency of convection-based vaporizing that is typically accomplished only with the larger, non-concealable, vaporizers. Embodiments of the invention provide a vaporizer that fits within a standard-sized pant pocket that conceals all functional components of the devices such that it resembles the shape of a smart phone. In addition, embodiments of the invention provide a device that dissipates the heat generated from the vaporization process quickly and efficiently before the vapor reaches the mouth of the user.

Figure 1:
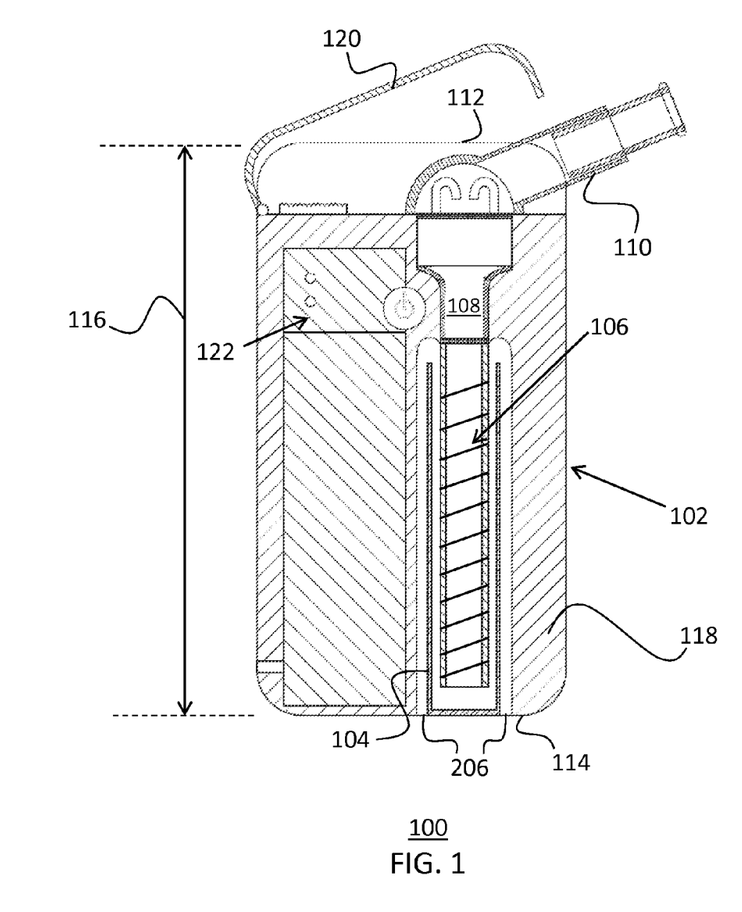
FIG. 1 is an elevational, partially cross-sectional, front view of a portable hand-held vaporizer assembly in accordance with the present invention.

Referring now to FIG. 1, one embodiment of the present invention is shown in an elevational, partially cross-sectional, view. The figures of the instant application show several advantageous features of the present invention, but, as will be described below, the invention can be provided in several shapes, sizes, combinations of features and components, and varying numbers and functions of the components. The first example of a portable hand-held vaporizer assembly 100, as shown in FIG. 1, includes a body 102, an air flow chamber 104, a heating element assembly 106, an herb placement zone 108, and a conductive conduit 110. At first glance, the shape of the body 102 can be readily appreciated to be much more discrete and compact than that of prior-art vaporizers generally known in the art. The body 102 is generally shaped to fit within a standard-sized clothing pocket so it can be easily transportable and not readily identifiable by the viewing public. A standard-sized clothing pocket generally ranges in dimensions approximately from 2×5 (width×height) inches to 8×10 inches. FIG. 1, along many other figures shown herein, is partially cross-sectional as only the portion of the body 102 with the airflow chamber 104, a portion of the heating element assembly 106, herb placement zone 108, and conductive conduit 110 is cross-sectional.

Figure 6:
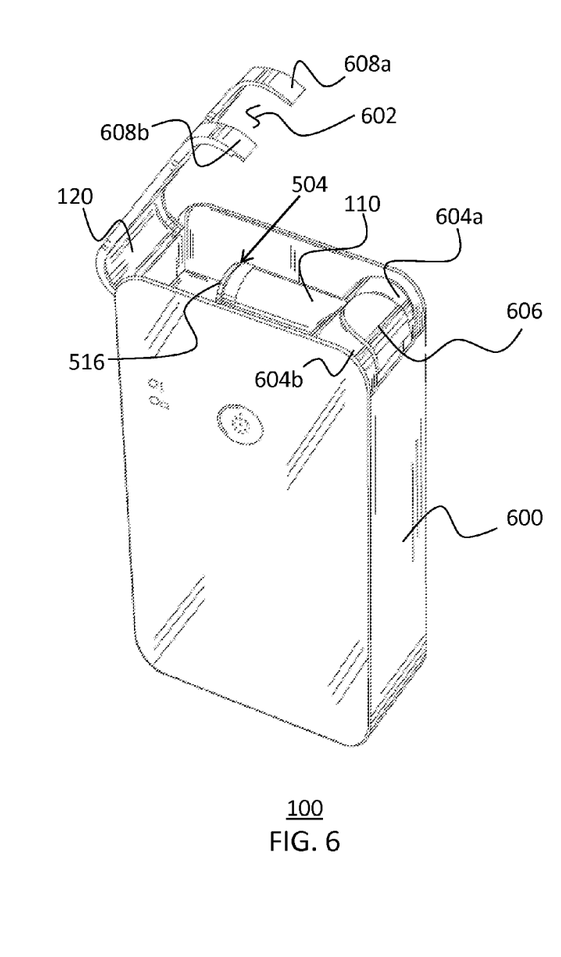
FIG. 6 is a perspective downward-looking view of the vaporizer of FIG. 1 illustrating a first position of a conduit that is substantially recessed within a body in accordance an embodiment of the present invention.

The body 102 can be seen having an upper end 112 and a lower end 114, opposite to the upper end 112, separated by a body height 116. In one embodiment, the body height 116 is at most approximately 6 inches to allow the assembly 100 to fit within a standard-sized clothing pocket and be transportable. In other embodiments, the body height 116 is greater than 6 inches, but sufficiently sized to be fitted within a standard-sized clothing, e.g., pants, pocket. The body 102 may also have a cover 120 which protects the inside of the body 102 and the conduit 110, should the conduit 110 be concealed within the body 102. The upper end 112 of the body 102 will therefore be the point on the body 102 where the cover 120 is in a closed position, rather than an open position—the closed position being exemplified in FIG. 1. In one embodiment, the body 102 is made completely from an outer shell of durable plastic. In other embodiments, the body 102 has portions, such as the front face 118 and back face (not shown), made of plastic or other heat resistant materials and the side portions 600 (one of which is shown in FIG. 6) of the body 102 made from metallic or other conductive materials. In yet further embodiments, the entire body 102, or portions thereof, may be made from a metallic, composite, ceramic, or other material or any of the above combinations.

As components of the heating element assembly 106 reach temperatures around 400 degrees Fahrenheit, portions of the body 102, where it is handled by a user, should be protected with a non-conductive material. The body 102 generally has four sides, which includes the front face 118, and two ends 112, 114 such that it surrounds what may be referred to herein as the body 102 "inner area." The inner area is generally where the components of the assembly 100 are at least partially encapsulated.

In one embodiment, the body 102 is in the general shape of a standard-sized cellular phone. A standard-sized cellular phone has dimensions generally ranging from 3.5×2×0.25 (body height×width×thickness) to 5.5×4×1. Now, a portable, convection-based vaporizer is available that assimilates those cellular phones presently available on the market. With the body 102 emulating the shape of a standard-sized cellular phone, the assembly 100 provides the user with the ability to transport and reveal the vaporizer 100 without the body 102 itself advertising that it is an herb-smoking-type apparatus. As there remains a contingency of the general public that scoff at the idea of smoking, regardless the desired herb, discreetness is much desired by many users. The portable vaporizer 100 may be sized to fall outside those specifications of standard-sized cellular phones, but should readily fit inside a pant pocket and has at least one configuration where the body 102 is in the general shape of a standard-sized cell phone.

Figure 2:
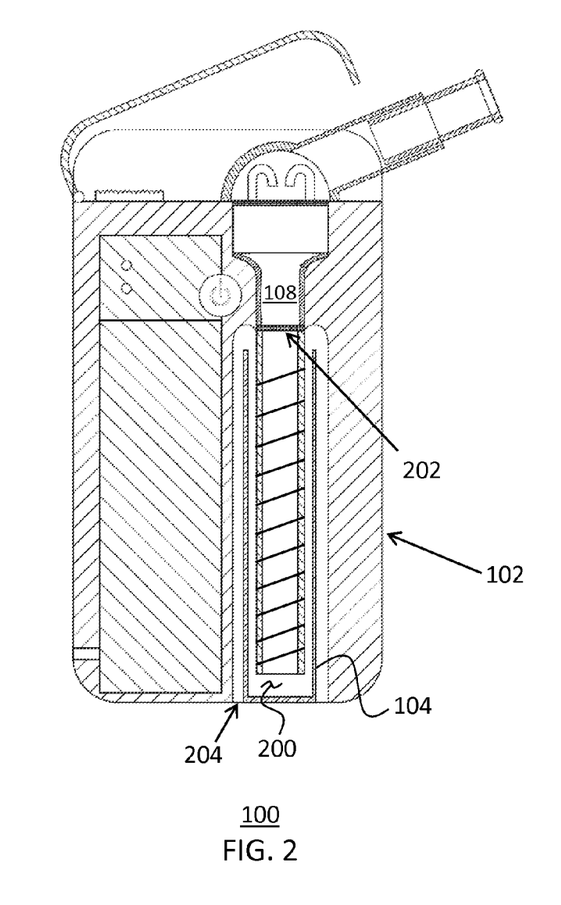
FIG. 2 is an elevational, partially cross-sectional, front view of the vaporizer assembly of FIG. 1 with an airflow chamber defining an airflow passage that is placed in fluid communication with a herb placement zone in accordance with the present invention.
Figure 3:
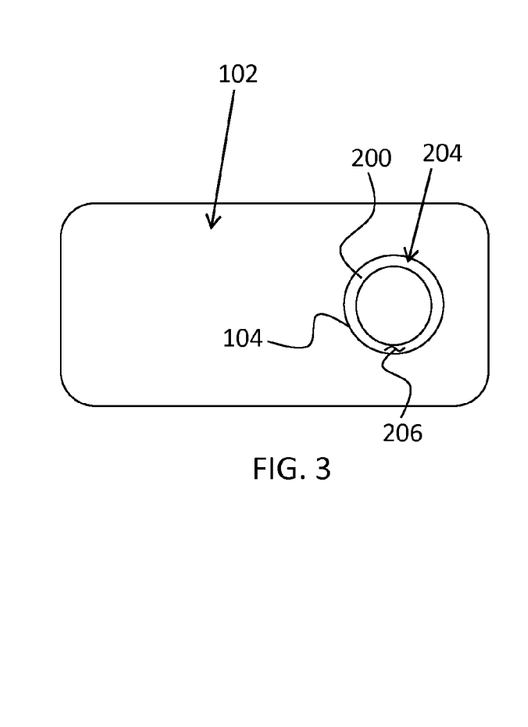
FIG. 3 is a bottom plan view of the vaporizer assembly of FIG. 1 with a distal end of the airflow chamber defining a distal opening that places the airflow passage in fluid communication with an outside environment in accordance with the present invention.

Referring now to both FIGS. 2 and 3, portions airflow chamber 104 can be seen will now be described in detail. Specifically, FIG. 2 illustrates a cross-section of the airflow chamber 104 which defines an airflow passage 200. FIG. 3 illustrates a bottom plan view of the body 102 showing the outside view of the airflow chamber 104 being in the general shape of a circle that generally extends upwardly through the body 102. In other embodiments, the airflow chamber 104 may be in the shape of a rectangle, may be slotted, or has apertures that extend upwardly through the body 102 and has at least a portion that reaches the herb placement zone 108. The airflow chamber 104 has a proximal end 202 and a distal end 204, opposite to the proximal end 202. The proximal end 202 can be seen adjacent to the herb placement zone 108. The distal end 204 of the chamber 104 defines a distal opening 206 that places the airflow passage 200 in fluid communication with an outside environment. The airflow passage 200 can be seen traveling through the chamber 104, into the herb placement zone 108, and out through the conduit 110. In one embodiment, the airflow chamber 104 may be formed integrally at least partially within the body 102 by using a mold. In other embodiments, the chamber 104 may be formed separately from the body 102 and coupled thereto with various attachments such was epoxy, clasps, and the like.

In one embodiment, the distal opening 206 (shown in FIG. 3) is directly adjacent to the outside environment, as shown in the figures, but it should not be necessarily limited as such. In other embodiments, the distal opening 206 is disposed at a location within the body 102 and the body 102 has one or more apertures from which the outside air is drawn. Further, the body 102 may also have a fan or blower that pulls outside ambient air into the distal opening 206, which may facilitate the user with inhaling the herb's active ingredients. Regardless the configuration, the distal opening 206 provides the assembly 100 with a steady stream of fluid, i.e. air, used for the convection heating process, which is more effective and efficient than other heating methods used by prior-art vaporizers. In one embodiment, the airflow chamber 104 is open at both ends 202, 204 such that it should not be considered completely enclosed. In other embodiments, the chamber 104 may be partially closed at the distal end 204, with a fan or blower therein.

Referring specifically to FIG. 2, the airflow chamber 104 is illustrated as completely encapsulated within the body 102. The term "encapsulated" is defined herein as having some portion lying in between the referenced structure, plane, or object. In other embodiments, portions of the airflow chamber 104 may extend outside the body such that the chamber 104 would still be said to be at least partially encapsulated within the body 102. It is preferable, however, that the chamber 104 be completely encapsulated to reduce and resist impacts that could compromise the chamber's integrity.

Figure 4:
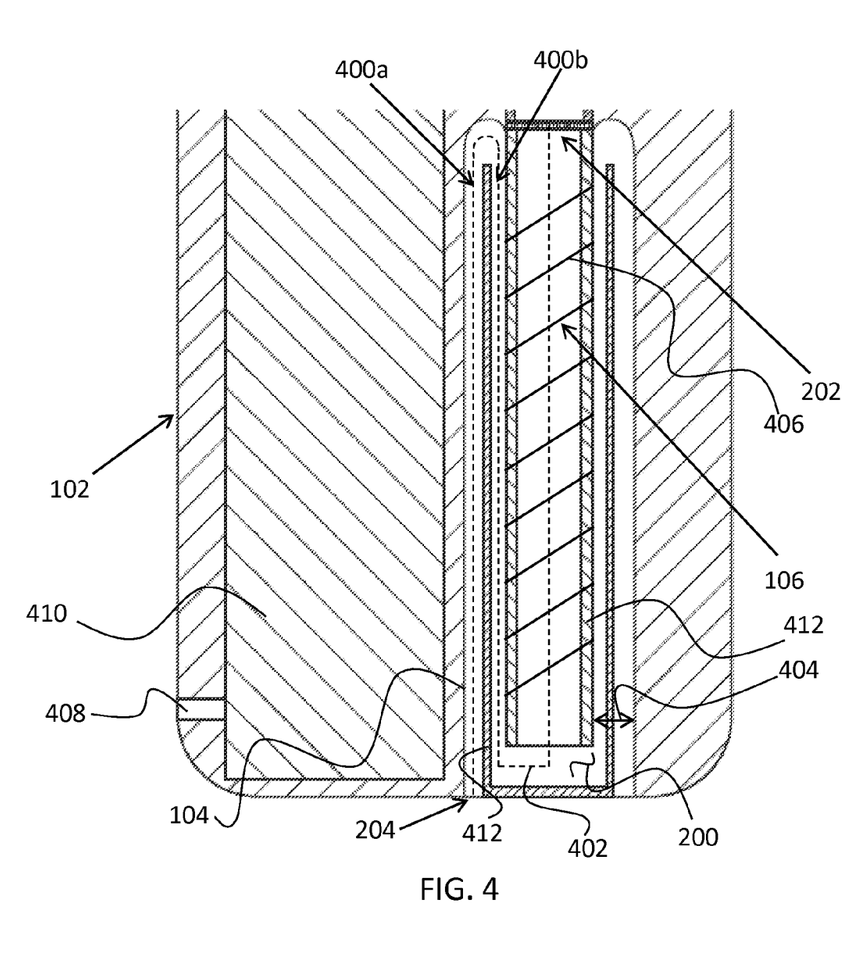
FIG. 4 is a close-up, elevational, partially cross-sectional, front view of the airflow chamber of FIG. 1.

To achieve the superior convection-based heating typically accomplished by larger, non-hand-held, vaporizers, the airflow chamber 104 is multidirectional. FIG. 4 illustrates a close-up view of the air flow chamber 104 in accordance with the present invention. As the body 102 is advantageously designed to fit within a standard-sized clothing, e.g., pant, pocket and the air is required to reach 350-400 degrees Fahrenheit, the airflow chamber 104 can be seen having at least two portions 400a-b along a chamber length that at least partially overlap one another. With the airflow chamber 104 defining an air path that directs the air in multiple directions, i.e., turning 180 degrees, the airflow passage 200 is thermally coupled longer to the heating element 106. Due to the compact design of the vaporizer assembly 100, the design of the airflow chamber 104, allows the incoming air to reach the effective vaporizing temperature without utilizing elongated chambers generally associated with prior hand-held convection-based vaporizers. In one embodiment, the chamber 104 can be seen incorporating one or more dividers 412 that separate the chamber 104 into different paths, i.e., "multidirectional," that effectively channel the incoming air, while utilizing as little distance as possible. In other embodiments, the chamber 104 may wrap around the actual heating element 406 such that the divider 412, which separates the chamber 104 into two channels in the opposite direction would, not be required.

The multidirectional—i.e. having a general direction changing in one or more angles—path defined by the chamber 104 provides the assembly with air with an effective and relatively constant vaporizing temperature when it reaches the herb placement zone 108.

The airflow chamber 104 has a longitudinal central axis that passes through a center of the chamber 104, i.e., substantially equidistant from all portions of an interior wall of the chamber 104, and is parallel to the direction of airflow when the assembly 100 is operated. This longitudinal central axis is represented by a dashed line 402 shown in the view of FIG. 4 and is also equivalent to the chamber length. As indicated with the dashed line 402, the chamber length extends from the distal end 204 to the proximal end 202 of the chamber 104. As mentioned, the chamber 104 may be in various configurations, i.e. slotted or having apertures, such that one side of the chamber 104, indicated with double arrows 404, may not be included. As such, the chamber length is defined as the length extending from just one portion of the distal end 204 to the proximal end 202. To effectively heat the airflow passage 200, in one embodiment, the chamber length is greater than the body height 116. With the ability of the airflow passage 200 to be thermally coupled to the heating element 106 for a longer period of time, the body 102 is able to be reduced to dimensions not previously accomplished with prior known, non-fueled, convection-based vaporizers.

Also shown in the FIG. 4 is the heating element assembly 106. The heating element assembly 106 has a portion, or an actual heating element 406, that is thermally coupled to the airflow passage 200 to reach the desired vaporizing temperature. The entire heating assembly 106, or one or more portions thereof, e.g. the heating element 406, may also be referred to as the "heat engine" or "heating engine" as it is this component that thermally charges the incoming outside ambient air to a proper vaporizing temperature. The term thermally coupled is defined as having a first and second object or matter in relative proximity such that heat is effectively exchanged from the first object to the referenced second object or matter. In one embodiment, the heating element 406 is a tungsten-based metallic alloy in the form of a coil that is disposed at least partially within the airflow passage 200. In other embodiments, the heating element 406 is made from nickel-chrome, other types of metals, or metal-based composites that have a general low thermal resistivity and are generally safe to pass air through for human consumption. In further embodiments, the heating element 406 may be in the form of a plate or other shape, and may be located within a piece of glass or in close proximity to the airflow passage 200, but yet still able to effectively transfer heat.

The heating element assembly 106 includes one or more batteries used to provide energy to the heating element 406 when in operation. The assembly 100 is designed to run on standard-sized batteries which includes lithium-ion based batteries. This is advantageous over prior known vaporizers that utilize fuel-based systems to heat the air to the vaporizing temperature because those fuel-based systems produce foul-tasting by-products and are generally loud and bring attention to the device. As such, the hand-held vaporizing assembly can be operated on 2.8 to 3.3 volts, with the possibility of recharging the batteries after continued use with an optional charging port 408. The charging port 408 may be located on the side of the body 102, as shown, or may be located on any other portion of the body 102. In such an embodiment, the batteries may charge with the assembly 100 operating fully on the supplied electricity from an outside source. The batteries are also at least partially encapsulated within the body 102 in a battery storage portion 410 of the body 102 (not shown). The voltage of any power source used with the present invention is in no way limited to any specific voltages or range of voltages.

Figure 5:
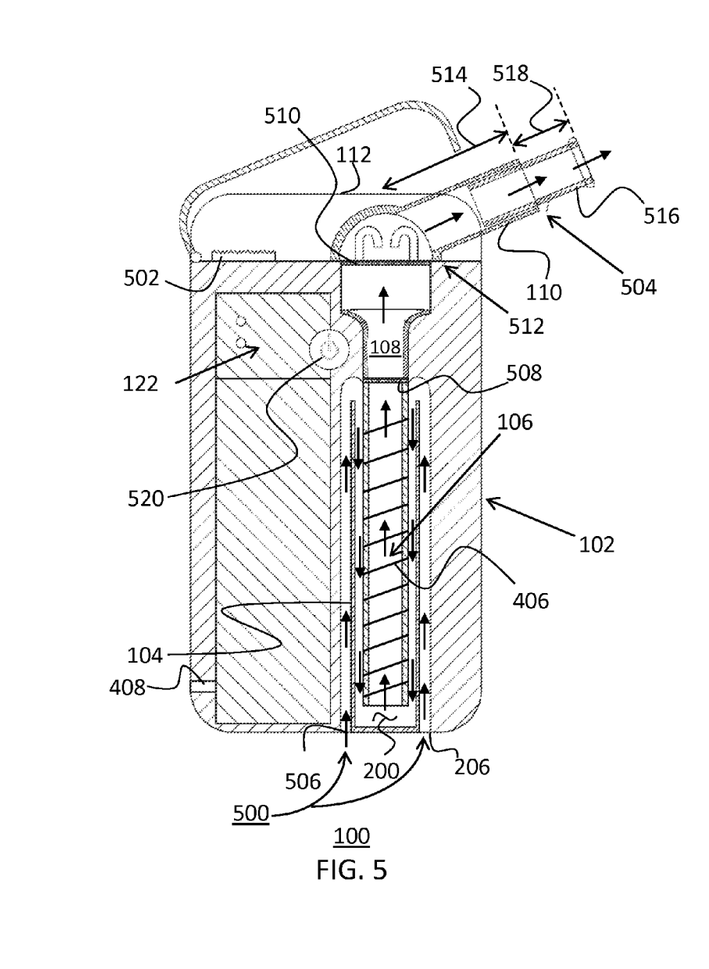
FIG. 5 is an elevational, partially-cross-sectional, front view of the vaporizer of FIG. 1 illustrating air traveling through the airflow chamber when the device is being operated in accordance with the present invention.

Referring now to FIG. 5, the assembly is shown again in an elevational front view. When in operation, the user turns on the device 100 which in turn supplies power to the heating element 406, for example, by depressing a button 520 on the front face of the device. After a period of time, the heating element 406 will have reached a temperature sufficient to transfer heat to airflow passage 200 in order for the air to reach a desired vaporizing temperature. In one embodiment, the heating element assembly 106 may come with a temperature dial 502 and/or a thermostat (not shown) for regulating the temperature of the heating element 406 or the temperature of the airflow passage 200. In other embodiments, the heating element 406 may be supplied power to reach a predetermined temperature or may have a display indicating to the user what the temperature is or that the device is ready for use. In one embodiment, all or at least a portion of the circuits, wiring, and other electronics are at least partially encapsulated within and located on an upper portion 122 of the body 102, shown in FIG. 1 as being directly above the battery compartment. In other embodiments, the aforementioned electronics are located in other areas of the body 102 and may have one or more portions partially exposed outside of the body 102.

In one embodiment, after the heating element 406 reaches the desired temperature, a user inhales from the air sealed conduit 110, which pulls the outside air 500 through the chamber 104 out through a distal end 504 of the conduit 110. The path of the air through the airflow passage 200, which is also referred to herein as the multidirectional airflow passage, is represented in the figure as a plurality of arrows 506. As the chamber 104 is relatively "air tight," when the user inhales on the distal end 504, the air chamber 104 inner pressure decreases and the outside ambient air 500, which is at a higher pressure, is forced into the distal opening 206. In other embodiments, air flows into the airflow passage 200 through the use of a fan or blower, as mentioned above.

FIG. 5 also illustrates the airflow passage 200 being in fluid communication with the herb placement zone 108. Just as it sounds, the herb placement zone 108 is where the user places the desired material to be vaporized. In one embodiment, the herb placement zone 108 has a screen 508 located at least partially in the path of the airflow passage 200 that separates the placement zone 108 from the airflow chamber 104. The screen 508, which is generally known in the art, allows air to enter and supports the herb, but resists the herb, or debris from the herb, from entering the airflow passage 200. In other embodiments, the herb placement zone 108 may not have a screen 508, such that the herb is supported by the side walls of the placement zone 108.

In one embodiment, an upper edge 510 of the herb placement zone 108 is at most approximately 2 inches away from a lower portion 512 of the conduit 110. This prevents the temperature of the vapor at the distal end 504 of the conduit 110 from varying based upon how fast or slow the user inhales which as symptomatic of those prior known vaporizers. In other embodiments, the upper edge 510 is greater than 2 inches away from the lower portion 512 of the conduit 110, but the configuration of the airflow chamber 104 might be required to be changed. Now a hand-held vaporizer has the ability to be small enough to fit within a clothing pocket, be in the shape of stand-sized cellular phone, and advantageously provides consistent inhale temperatures regardless of the inhale rate of the user.

In FIG. 5, the conduit 110 is shown placing the airflow passage 200 in fluid communication with the outside environment. To conceal the purpose of the assembly 100, leaving it relatively unidentifiable to the viewing public, the conduit 110 has a first position where the distal end 504 is at least partially within the body 102 (shown in FIG. 6) and a second position where the distal end extends a length 514 away from the body 102 (shown in FIG. 5). As the conduit 110 has two positions it serves two goals of the present invention, which are to be discrete and to have a small convection-based vaporizer that generates vapor at a consistent and safe temperature. In one embodiment, the length 514 is approximately 2 inches. In other embodiments, the length 514 will vary depending on what position the conduit in, but should be a length 514 sufficient such that it fits within the confines of the body 102. As such, the conduit would be said to be placed substantially within the body 102. Although in certain embodiments of the invention, the conduit 110 may be completely concealed or recessed within the body 102 when in the first position, it should not be so limited. In other embodiments, portions of the conduit 110, including the distal end 504, may slightly protrude outside the body 102. Generally, however, most portions of the conduit 110 should be placed within the body 102, when in the first position, to prevent damage and so the assembly does not attract attention.

In one embodiment, to effectively expel heat generated from the vaporization process, the conduit 110 is conductive, or has the ability to transfer heat across the material at a generally high rate. In one embodiment, the conduit 110 is made from a metal, such as aluminum or copper. In other embodiments, the conduit 110 is made from conductive polymers, composites, or other metallic-based materials with conductive properties. As the herb placement zone 108 is generally close to conduit 110, the conduit 110 plays the important role of reducing the vapor temperature. As the vapor travels through the conduit 110, it is in contact with the inner surface of the conduit 110 thereby reducing the temperature so it can be subsequently inhaled by the user. The conduit 110 may also have one or more portions that are not conductive, to allow a user to comfortably place the conduit 110 in the first position within the body 102.

FIGS. 5 and 6 also illustrate the conduit 110 having a substantially non-conductive mouthpiece 516 coupled to the conduit 110. As the mouthpiece 516 is non-conductive, a user can safely place his or her mouth on the mouthpiece 516 to create a "suction effect" and inhale the generated vapors. In one embodiment, the mouthpiece 516 is made with glass, which may or may not be transparent, and is disposed at least partially within the distal end 504 of the conduit 110. In other embodiments, the mouthpiece 516 is made from a non-conductive polymer or other non-conductive material that resists the transfer of heat through the material. In other embodiments, the mouthpiece 516 may also overlap the distal end 504 of the conduit 110 and be telescopic. To prevent a user from touching the distal end 504 of the conduit 110 during operation of the assembly 100 and to facilitate storing the conduit 110 within the body 102, the mouthpiece 516 is adjustable a variable length 518 away from the distal end 504 of the conduit 110. Regardless of the embodiment, the mouthpiece 516 creates an "air tight" seal with the conduit to prevent vapors from escaping.

Specifically referring now to FIG. 6, the cover 120 is shown coupled to the body 102 and being removably-couplable to a portion of the conduit 110 when the conduit 110 is in either the first or second position. The purpose of the cover 120 is two-fold. First, it protects the components disposed within the body 102 and the conduit 110 from outside impact and environmental debris or liquid. Second, it serves as another heat sink that facilitates in reducing vapor temperature before it is inhaled by the user. As such, in one embodiment, the cover 120 is made from a conductive material, similar to those described for the conduit 110. In other embodiments, the cover 120 is only rotatable to allow the conduit 110 to move from the first to the second position and may be generally non-conductive. In further embodiments, the cover 120 has a portion 602 shaped to receive the conduit 110 when it is in either the first and second position so there is one or more coupling contact points with the conduit 110.

Figure 7:
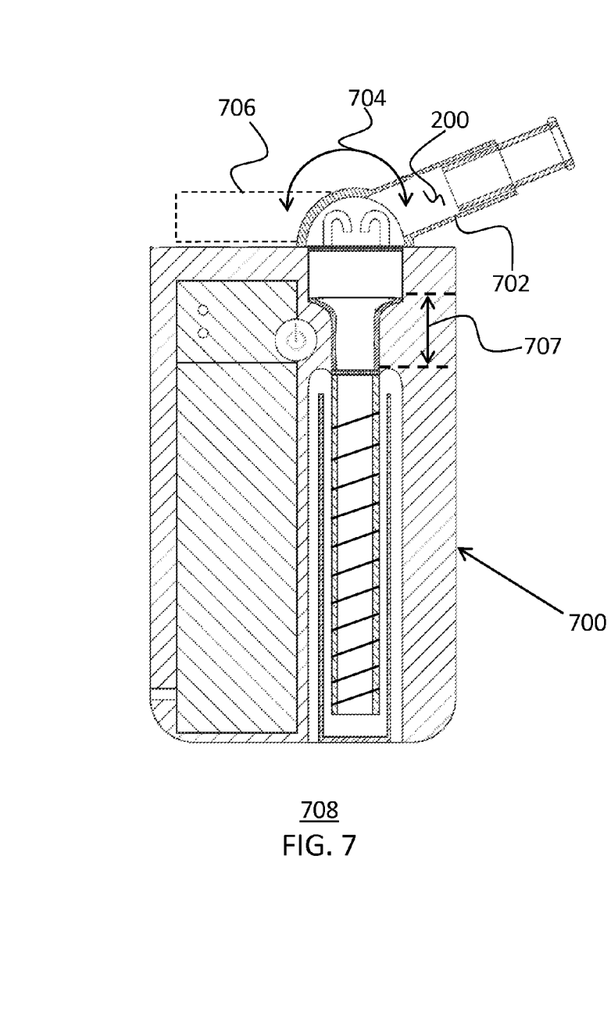
FIG. 7 is an elevational, partially cross-sectional front, view of a conduit being rotatable along a rotation path from a first position that is substantially recessed within the body to a second position where a distal end of the conduit extends a length away from the body in accordance with an exemplary embodiment of the present invention.

Referring now to both FIGS. 6 and 7, FIG. 7 illustrates one embodiment of the present invention with the cover 120 and top portion of the body 700 removed. In one embodiment, the conduit 702 is rotatable along a rotation path 704 defined by the conduit 702 to either the first or second position. The first position 706 of the conduit 702 is shown in FIG. 7 with dashed lines. In one such method, the conduit 702 has two portions 604a-b that are non-rotatable and a center spout portion 606 which would rotate in between the two portions 604a-b (shown in FIG. 6) having air tight seals in between to substantially prevent vapor from escaping. To further facilitate reducing the vapor temperature, the two portions 608a-b of the cover 120 are removably-couplable to and mate with the corresponding two portions 604a-b of the conduit 702, respectively. The conduit 702 may also be rotatable using other methods that do not compromise the integrity of the airflow passage 200, such that vapor would not escape.

The rotation path 704 may be in the form a variety of different non-linear paths and various planes, both horizontal and vertical. If the assembly 708 is only rotatable then the device might provide access to the herb placement zone 108 through other methods, such as removing or opening a portion 707 of the body 700. Now, the assembly 100 can be quickly and effectively converted from a device, most of the viewing public would perceive as cellular phone, to an effective and efficient convection-heated vaporizer assembly 708.

Figure 8:
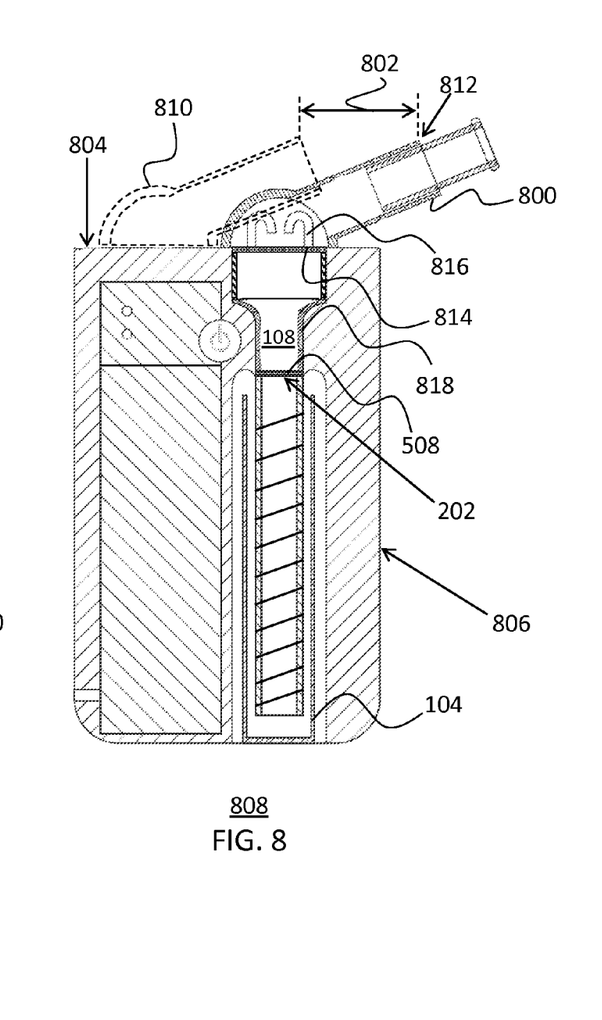
FIG. 8 is an elevational, partially cross-sectional, front view of a conduit being operable to be rotatable along a rotation path and slidable along a translation path in accordance with another embodiment of the present invention.

There are multiple variations or configurations of the conduit 110 that are within the spirit and scope of this invention. FIG. 8 illustrates another embodiment the conduit 800. In FIG. 8, the conduit 800 is both slidable and rototable. As with the embodiment of FIG. 7, the conduit 800 may be rotatable to the first position 706, but may also be slidably-placed into the first position. The conduit 800 is slidable along a translation path 802 defined by the conduit 800 (shown by the arrow). Although the conduit 800 is shown translating laterally, or left to right, it should not be limited as such. The conduit 800 may also translate, or rotate, horizontally along a thickness 1000 (shown in FIG. 10) of the body 806. FIG. 8 illustrates how the conduit 800 may be moved to the left, or a third position 810 (indicated with dashed lines), that at least partially exposes the herb placement zone 108. The conduit 800 may be translated using one or more tracks, which would unlock to move the conduit 800 and lock into place when the assembly 808 is in operation. The conduit 800 would then need to be rotated slightly along the rotation path 704 (shown in FIG. 7) to provide better access to the herb placement zone 108.

To provide better access to the herb placement zone 108, in one embodiment the assembly 808 has an upper screen 814 has one or more hooks 816. The upper screen 814 prevents any herb located within the zone 108 from being removed when the user draws on the conduit 800 or when the assembly 808 is turned upside-down. The hook(s) 816 facilitate the removal of the upper screen 814, but are not necessarily required. In other embodiments, the screen 814 may be connected to a removable side wall 818 that defines the herb placement zone 108. As described, the hooks 816 would remove the side wall 818 to allow a user to clean and/or refill the herb placement zone 108. The side wall 818 may also be connected to the screen 508 adjacent to the proximal end 202 of the airflow chamber 104 such that access to the chamber 104 may be accomplished. In further embodiments, the body 806 may not have any upper screen 814 such that the assembly 808 may be turned upside-down and the herb is forcibly removed.

In further embodiments of the present invention, the conduit 800 may not be rotatable, but is rather placed into the first and second positions by sliding the conduit 800 along or more tracks, as described. As such, a top portion 804 of the body 806 would be sufficiently spaced to allow the conduit to translate laterally through the translation path 802. When in the first position, the herb placement zone 108 would then be open to the outside environment, such that a cover 120 (as shown in FIG. 6) would be preferably utilized. When the user desires to use the assembly 808, the user would slide the conduit 800 over the herb placement zone 108, thereby creating a substantially air tight seal and extending a distal end 812 of the conduit 800 away from the body 806.

Figure 9:
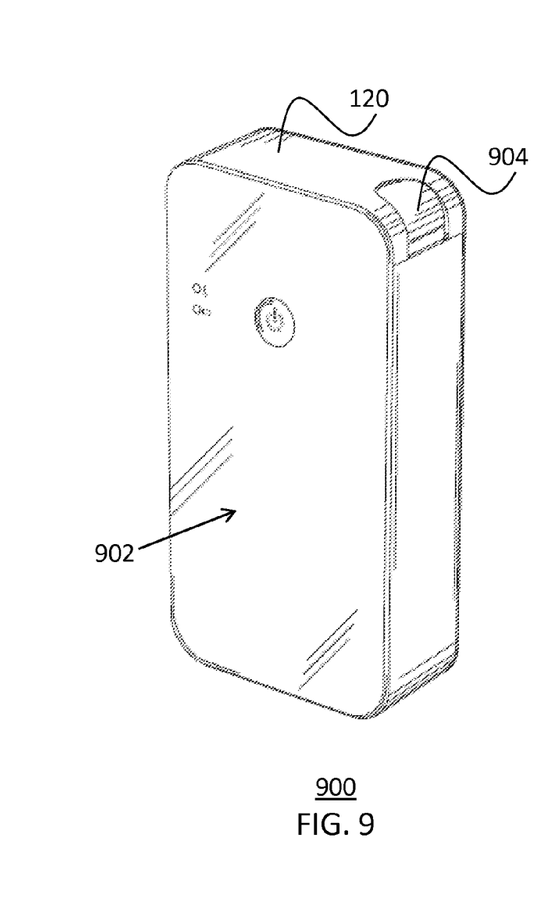
FIG. 9 is a perspective downward looking view of a vaporizing assembly illustrating the conduit being placed in a first position that is substantially recessed within the assembly body in accordance an embodiment of the present invention.
Figure 10:
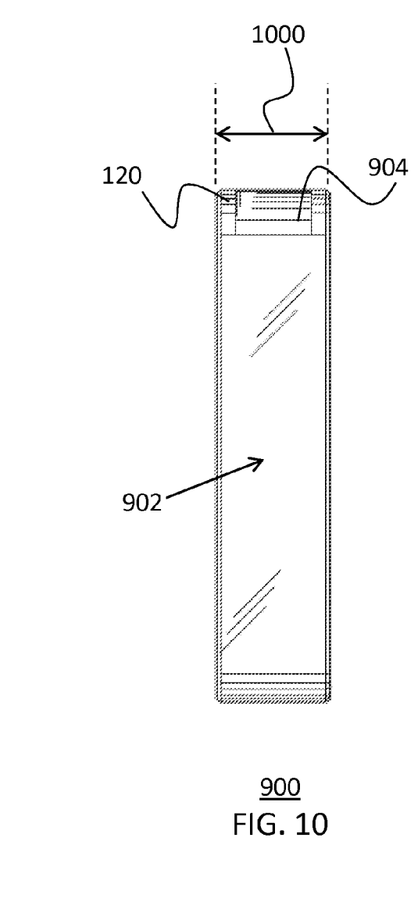
FIG. 10 is an elevational side view of the assembly of FIG. 9 with the conduit in the first position in accordance an embodiment of the present invention.
Figure 11:
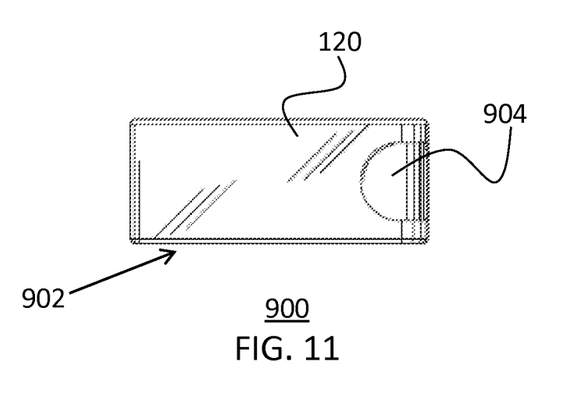
FIG. 11 is a top plan view of the assembly of FIG. 9 with the conduit in the first position in accordance an embodiment of the present invention.

FIGS. 9-12 illustrate examples of the assembly 900 in various views as the conduit 904 is placed both in the first and second positions in accord with embodiments of the present invention. FIG. 9 shows the assembly 900 with the conduit 904 completely recessed within the body 902. The cover 120 can also be seen overlaying the conduit 110 to provide further protection to the conduit 904 and other components located within the body 902 of the assembly 900. FIG. 10 shows the assembly 900 at an elevational side view, also with the conduit 904 completely recessed within the body 902. FIG. 11 shows the assembly 900 from a top plan view, with the conduit 904 completely recessed within and the cover 120 substantially enclosing the conduit 904. FIGS. 9-11 demonstrate the advantageous compact and unassuming nature of the assembly 900 that is relatively inconspicuous to the public as a convection-based vaporizer.

Figure 12:
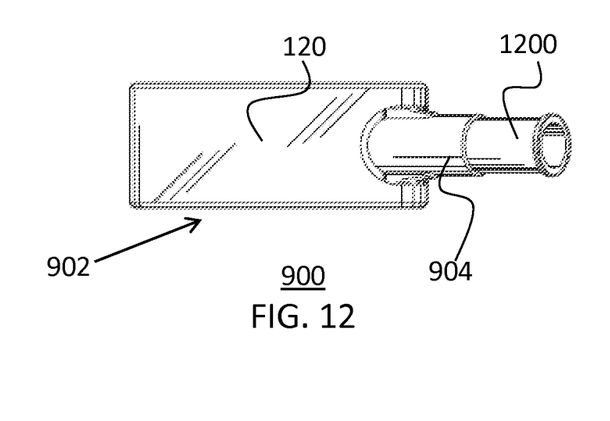
FIG. 12 is a top plan view of the assembly of FIG. 9 illustrating the conduit being placed in a second position where the distal end extends a length away from the body in accordance with another embodiment of the present invention.
Figure 13:
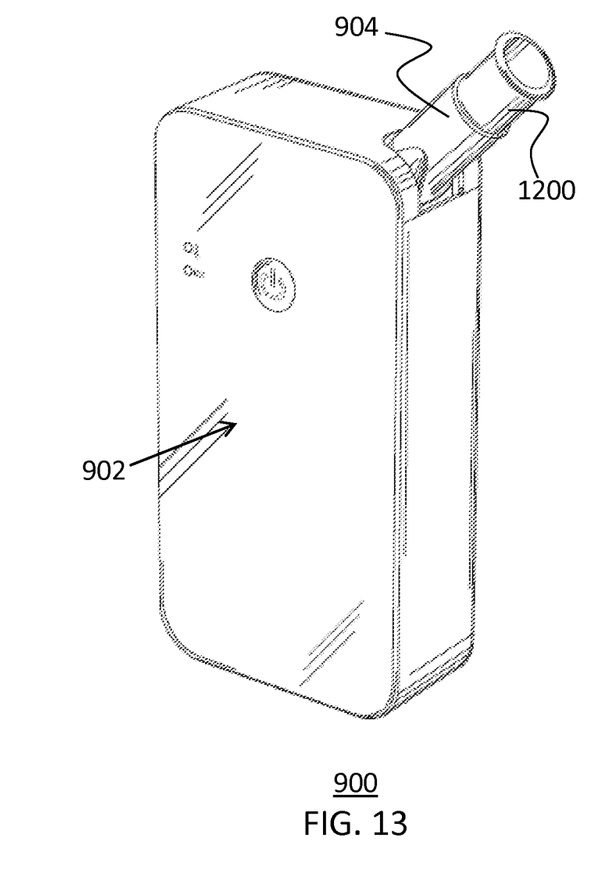
FIG. 13 is a perspective downward-looking view of the assembly of FIG. 9 with the conduit in the second position in accordance with an embodiment of the present invention.

FIGS. 12 and 13 illustrate one embodiment of the assembly 900 while the conduit is in the second position extending away from the body 902. Specifically, FIG. 12 shows the assembly 900 from a top plan view with the cover 120 enclosed on conduit 904 to prevent any debris from entering the body 904. As previously mentioned, the cover 120 also serves as a heat sink for the vapor passing though the conduit 904. Both figures also illustrate the mouthpiece 1200 disposed at least partially within the conduit 904 in accord with an embodiment of the present invention.

A portable hand-held vaporizer has been disclosed that provides a body in the shape that is able to fit within a standard-sized pant pocket and also resembling a standard-sized cellular phone. This novel vaporizer utilizes the more effective and efficient convection-based heating while still maintaining a compact design. To achieve this, the vaporizer discloses an airflow chamber directing outside ambient air through a heating element into an herb placement zone, which is located in the near proximity to a distal end of a conduit where it is subsequently inhaled by a user. When the vapor reaches the user, the temperature has reduced to a range that is safe and comfortable for the user. The vaporizer further provides that the conduit may be advantageously placed in a first and second position that allows the purpose and nature of the device to be relatively unidentifiable to the viewing public.

What is claimed is:

1. A portable hand-held vaporizer assembly comprising:
a body shaped to fit substantially within a standard-sized clothing pocket, the body including:
an airflow chamber defining an airflow passage, the air flow chamber:
having a proximal end and a distal end, opposite to the proximal end, the distal end defining a distal opening that places the airflow passage in fluid communication with an outside environment; and
being at least partially encapsulated within the body;
a heating assembly with a convection-based heating element, the convection-based heating element having a portion thermally coupled to the airflow passage;
an herb placement zone downstream from the convection-based heating element and in fluid communication with the airflow passage; and
a conductive conduit that places the airflow passage in fluid communication with the outside environment, the conduit having a first position where a distal end of the conduit is substantially placed within the body and a second position where the distal end extends a length away from the body.

2. The portable hand-held vaporizer assembly according to claim 1, wherein the body further comprises:
an upper end;
a lower end, opposite to the upper end; and
a body height separating the upper and lower end that is at most approximately 6 inches.

3. The portable hand-held vaporizer assembly according to claim 1, wherein:
the body is in the general shape of a standard-sized cellular phone.

4. The portable hand-held vaporizer assembly according to claim 1, wherein the herb placement zone further comprises:
a screen that separates the herb placement zone from the airflow channel; and
an upper edge that is at most approximately 2 inches away from a lower portion of the conduit.

5. The portable hand-held vaporizer assembly according to claim 1, wherein:
the airflow passage directs air heated by the convection-based heating element into the herb placement zone.

6. The portable hand-held vaporizer assembly according to claim 1, wherein the conduit further comprises:
a substantially non-conductive mouthpiece coupled to the conduit.

7. The portable hand-held vaporizer assembly according to claim 6, wherein:
the substantially non-conductive mouthpiece is adjustable a variable length away from the distal end of the conduit.

8. The portable hand-held vaporizer assembly according to claim 1, wherein the body further comprises:
a cover that is coupled to the body and removably-couplable to a portion of the conduit when the conduit is in at least one of the first and second positions.

9. The portable hand-held vaporizer assembly according to claim 8, wherein:
the cover is rotatable and made from a conductive material.

10. The portable hand-held vaporizer assembly according to claim 1, wherein:
the conduit is rotatable along a rotation path defined by the conduit to at least one of the first position and the second position.

11. The portable hand-held vaporizer assembly according to claim 1, wherein:
the conduit is slidably-rotatable to at least one of the first position and the second position.

12. The portable hand-held vaporizer assembly according to claim 1, wherein:
the conduit is slidable along a translation path defined by the conduit to at least one of the first position and the second position.

13. The portable hand-held vaporizer assembly according to claim 1, wherein:

the conduit is operable to be placed in a third position that at least partially exposes the herb placement zone.

14. A portable hand-held vaporizer assembly comprising:
a body shaped to fit substantially within a standard-sized clothing pocket including:
a multidirectional airflow chamber defining a multidirectional airflow passage, the multidirectional airflow chamber:
having a proximal end, a distal end, opposite to the proximal end, and a chamber length separating the proximal and distal ends, the distal end defining a distal opening that places the multidirectional airflow passage in fluid communication with an outside environment;
having at least two separate portions along a chamber length that at least partially overlap one another; and
being at least partially encapsulated within the body;
a heating element assembly with a convection-based heating element, the convection-based heating element having a portion thermally coupled to the multidirectional airflow passage;
an herb placement zone downstream from the convection-based heating element and in fluid communication with the multidirectional airflow passage; and
a conductive conduit that places the multidirectional airflow passage in fluid communication with the outside environment.

15. The portable hand-held vaporizer assembly according to claim 14, wherein the body further comprises:
a lower end;
an upper end, opposite to the lower end; and
a body height separating the lower end and the upper end, wherein the chamber length is greater than the body height.

16. The portable hand-held vaporizer assembly according to claim 14, wherein the body further comprises:
a lower end;
an upper end, opposite to the lower end; and
a body height of at most approximately 6 inches separating the lower end and the upper end.

17. The portable hand-held vaporizer assembly according to claim 16, wherein:
the conduit has a first position where a distal end of the conduit is placed substantially within the body and a second position where the distal end extends a length away from the body.

18. The portable hand-held vaporizer assembly according to claim 14, wherein the herb placement zone further comprises:
a screen that separates the herb placement zone from the heating element; and
an upper edge portion that is at most approximately 2 inches away from a lower edge portion of the conduit.

19. A portable hand-held vaporizer assembly comprising:
a body defining an inner area, the body:
having a lower end, an upper end, and a body length of at most approximately 6 inches separating the lower end and upper end;
including a multidirectional airflow chamber defining a multidirectional airflow passage, the multidirectional airflow chamber:
having a proximal end and a distal end, opposite to the proximal end, the distal end defining a distal opening that places the multidirectional airflow passage in fluid communication with an outside environment; and
being at least partially encapsulated within body;
including a heating element assembly with a convection-based heating element, the convection-based heating element having a portion thermally coupled to the multidirectional airflow passage;
including an herb placement zone downstream from the convection-based heating element and in fluid communication with the multidirectional airflow passage; and
including a conductive conduit coupled to the body that places the multidirectional airflow passage in fluid communication with the outside environment, the conduit being operable to be at least one of slidable and rotatable to a first position where the body substantially conceals the conduit and a second position where the conduit extends outwardly away from the inner area.

20. The portable hand-held vaporizer assembly according to claim 19, wherein the body further comprises:
a cover that is coupled to the body and removably couplable to a portion of the conduit when the conduit is in at least one of the first and second positions.

\* \* \* \* \*